(12) United States Patent
Kulawiec et al.

(10) Patent No.: US 8,706,523 B2
(45) Date of Patent: Apr. 22, 2014

(54) METHODS AND SYSTEMS FOR TREATMENT REGIMEN MANAGEMENT

(75) Inventors: Julie T. Kulawiec, St. Charles, MO (US); Elizabeth W. Tooley, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 149 days.

(21) Appl. No.: 13/251,617

(22) Filed: Oct. 3, 2011

(65) Prior Publication Data

US 2013/0085767 A1   Apr. 4, 2013

(51) Int. Cl.
G06F 19/00  (2011.01)

(52) U.S. Cl.
CPC .................................. G06F 19/3456 (2013.01)
USPC .......................................................... 705/2

(58) Field of Classification Search
USPC ....................................... 705/2, 14.4; 53/474
See application file for complete search history.

(56) References Cited

U.S. PATENT DOCUMENTS

| | | | |
|---|---|---|---|
| 5,612,869 | A | 3/1997 | Letzt et al. |
| 7,956,727 | B2 | 6/2011 | Loncar |
| 2008/0238666 | A1 | 10/2008 | Loncar |
| 2011/0000170 | A1* | 1/2011 | Burg et al. ............ 53/474 |
| 2011/0225004 | A1* | 9/2011 | Loncar ............... 705/2 |
| 2012/0173319 | A1* | 7/2012 | Ferrara ............. 705/14.4 |

OTHER PUBLICATIONS

FactorTrack Mobile App—Living with Hemophilia, http://www.livingwithhaemophilia.com/webapp/livingfit/articles/factortrack-mobile app.jsp, Bayer Healthcare Pharmaceuticals, Inc., 2011, 2 pgs.
Intelecare—Personal Reminders—Reminder Solutions for Patents and Caregivers, iPad Edition, http://www.intelecare.com/products/ipad.php, 2005-2011. Intelecare Compliance Solutions, Inc., 2 pgs.
CareSpeak Communications, http://www.carespeak.com/news, 2011 CareSpeak Communications, Inc., 1 pg.
Intelecare—Personal Reminders—Reminder Solutions for Patents and Caregivers, iPhoneEdition, http://www.intelecare.com/products/iphone-ipodtouch.php, 2005-2011. Intelecare Compliance Solutions, Inc., 2 pgs.
Willig G, et al., "Design and Process Development for Smart Phone Medication Dosing Support System and Educational Platform in HIV.AIDS-TB Programs in Zambia," Integrated Design and Process Technology, IDPT 2009, 4 pgs.
MotionApps for Health, "Medication Adherence",CSI, HIV Medication Adherence, http://www.motionphr.com/medicationadhreence.html, Communication Software, Inc. 2009, 1 pg.
Red Ribbon Screen Shots, http://www.theredribbon.info/screenRR.html, 5 pgs.

(Continued)

*Primary Examiner* — John Pauls
(74) *Attorney, Agent, or Firm* — Randy L. Canis

(57) ABSTRACT

Methods and systems for treatment regimen management are described. In one embodiment, a treatment regimen associated with a user is determined. The treatment regimen includes treatment first treatment component and a second treatment component. The treatment regimen also includes a first treatment schedule associated with the first treatment component and a second treatment schedule associated with the second treatment component. Multiple treatment events are scheduled in an electronic calendar. The treatment events are based upon the first treatment schedule and the second treatment schedule. A treatment alert associated with each of the treatment events is generated. Other methods and systems are also described.

19 Claims, 14 Drawing Sheets

(56) References Cited

OTHER PUBLICATIONS

Mobile Apps for Health, "Smartphone Medication Reminders", CSI, Mobile Apps for Health management, Smartphone Medication Reminders, http://www.motionphr.com/Smart_med_reminders.html, 2 pgs.

Specialty Pharmacy News, "New Hepatitis C. Drugs Offer Much-Needed Options But With Asses Complications", Atlantic Information Services, vol. 8(9), Sep. 2011, 3 pgs.

* cited by examiner

METHODS AND SYSTEMS FOR TREATMENT REGIMEN MANAGEMENT

TECHNICAL FIELD

The present disclosure generally relates to treatment management, and more particularly to the use of mobile devices to manage treatment regimens.

BACKGROUND

Many diseases are treated with courses of treatment that can involve several different prescription drugs that should be taken at specific intervals. For example, new prescription drugs have come into the market for the treatment of hepatitis C. These drugs include boceprevir and teleprevir, and can have a complex treatment regiment identified by a doctor.

DETAILED DESCRIPTION

Example methods and systems for treatment regimen management are described. In the following description, for purposes of explanation, numerous specific details are set forth in order to provide a thorough understanding of example embodiments. It will be evident, however, to one of ordinary skill in the art that embodiments of the invention may be practiced without these specific details.

The treatment of some diseases or ailments may utilize relatively complex treatment regimens that may involve multiple treatments. The treatments may include medications of various types and administration modalities, such as injections, or administration, or the like. For example, some treatment regimens for hepatitis C, HIV, as well as other diseases and/or ailments, may utilize three or more different medications that have different administration modalities, including injection and oral administrations that may be undertaken at different intervals and over different time periods. The efficacy of the treatment may require relatively consistent compliance to the treatment regimen. That is, the efficacy of the treatment may require that the patient generally follow the treatment regimen, in terms of consistently undertaking the prescribed treatments in manner and at the times recommended by the treatment regimen. The methods and systems may generally be used to assist a person who is undergoing a treatment regiment to manage the various medications, tests and other aspects of their treatment. Each of the various aspects of the treatment regimen, including medications and tests, are commonly referred to as a treatment herein.

In some embodiments, treatments associated with the treatment regimen may be scheduled through a mobile electronic device or portable communication device, and reminders, or other indicators, of a scheduled treatment may be received.

In some embodiments, the ability to schedule treatments and receive reminders or indicators of a scheduled treatment may increase compliance with a treatment regimen. Therefore, a patient undertaking a complicated treatment regimen may be more likely to adhere to the treatment regimen and receive successful treatment.

Figure 1:
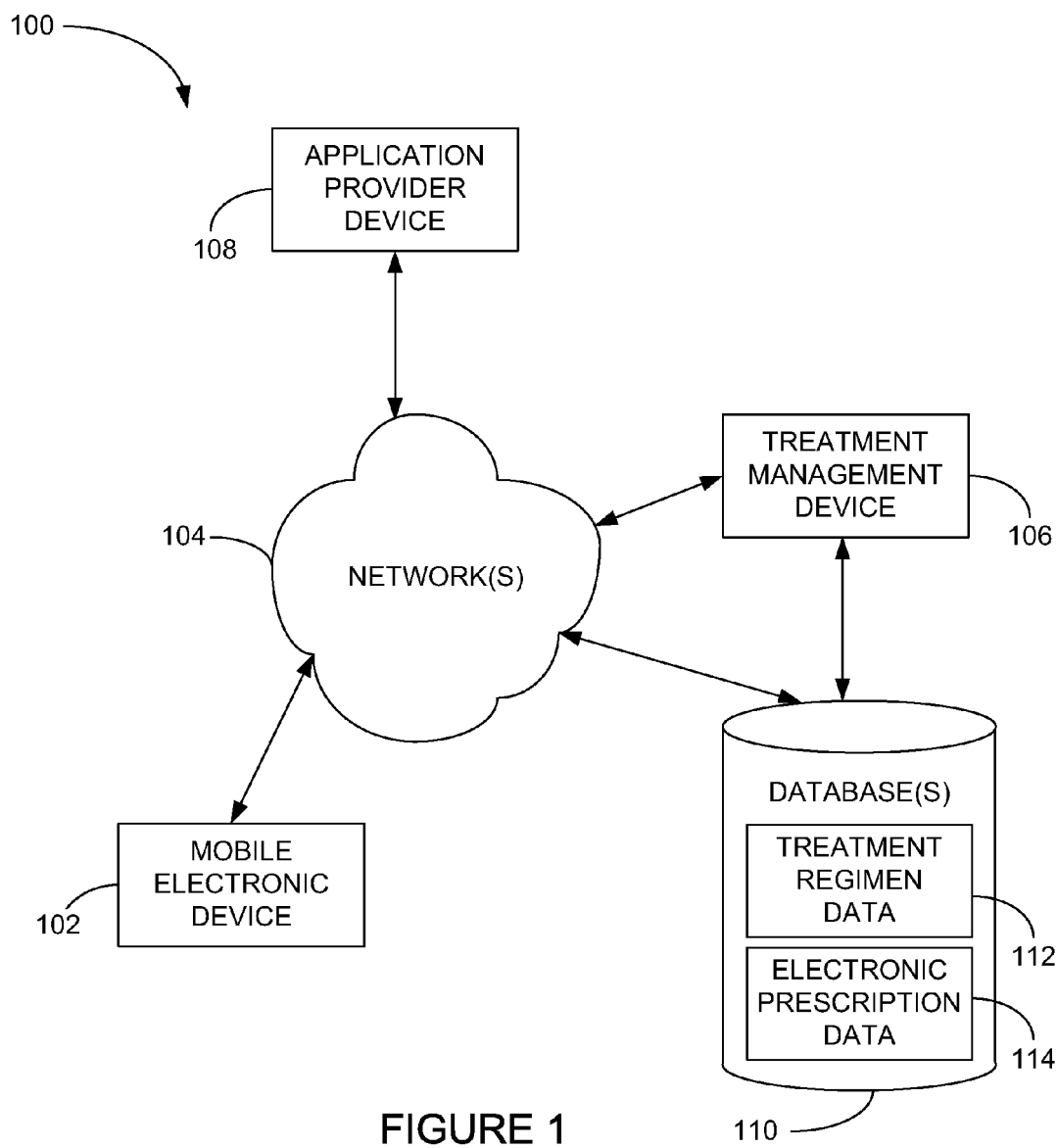
FIG. 1 is a block diagram of an example system, according to an example embodiment.

FIG. 1 is a block diagram of an example system 100, according to an example embodiment. The system 100 is an example environment in which treatments may be scheduled and indications of a treatment may be received. The system 100 includes a mobile electronic device 102 in communication with a treatment management device 106 over a network 104.

The mobile electronic device 102 is generally used to facilitate management of a treatment regimen by a device operator. The device operator may be a patient undergoing a treatment regimen. However, the device operator may be another person operating the mobile electronic device 102 on behalf of the patient. Examples of such people include parents, guardians and caregivers. Accordingly, while some illustrative embodiments may be described herein in which the device operator may be the patient, it should be appreciated that the device operator may be an individual other than the patient.

In some embodiments, the patient may utilize the mobile electronic device 102 manage the treatment regimen to assist them in undertaking the appropriate treatment at the appropriate time, according to a treatment schedule defined, at least in part, by the treatment regimen. For example, some treatment regimens may require multiple medications, or treatments such as lab tests, to be undertaken at designated times and/or on a continuous or regular basis over a defined period of time.

The mobile electronic device 102 may be a stand-alone device that solely provides at least some of the functionality to enable treatment regimen management, or may be a multi-use device that has functionality outside of treatment regimen management as described herein. Examples of the mobile electronic device 102 include an IPHONE device by Apple, Inc., mobile electronic devices powered by ANDROID by Google, Inc., and a BLACKBERRY device by Research In Motion Limited. Other types of mobile electronic devices may also be used. These can include, but are not limited to, portable computing devices and portable communication devices.

The network 104 by which the mobile electronic device 102 communicates with the treatment management device 106 may include, by way of example, Global System for Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

In some embodiments, a mobile application, or app, may be downloaded, installed, and launched on the mobile electronic device 102 to enable the device operator to access the treatment regimen management functionality. In an embodiment, the mobile application may also be referred to as a treatment management app. In some embodiments, some or all of the functionality discussed with respect to the treatment management app may be implemented, in whole or in part, via hardware.

The treatment management app may take advantage of hardware and/or software functionality provided by manufacturers of the mobile electronic device 102 and/or developers of the operating system of the mobile electronic device 102. For example, the treatment management app may use and/or interact with an electronic calendar, for example a calendar application of the mobile electronic device 102. The treatment management app may include instructions that when executed on the mobile electronic device 102 or in the treatment management device 106 cause a machine to change its state or perform tasks within the machine and with other machines. Further, in some embodiments, the treatment management app may interact with an electronic calendar, for example a calendar application, executed on another device, such as a cloud based calendar application. An example of such a calendar application may include GOOGLE Calendar, or other web-based, or network accessible, calendar application.

The treatment management app may be downloaded from an application provider device 108 or directly from the treatment management device 106. In general, the application provider device 108 is an entity that makes available mobile applications created by the application provider and/or third parties (e.g., the network manager) for download and use on mobile electronic devices. Examples of companies that operate the application provider device 108 include Apple, Inc. through its operation of ITUNES STORE, Google, Inc. through its operation of ANDROID MARKET, AT&T through its operation of its APPCENTER, and Research In Motion Limited through its operation of BLACKBERRY APP WORLD. Each of these application provider device companies can host and supply proprietary apps, open apps, and apps by third parties.

The mobile electronic device 102 may be in a client-server relationship with the treatment management device 106 and/or the application provider device 108, a peer-to-peer relationship with the treatment management device 106 and/or the application provider device 108, or in a different type of relationship with the treatment management device 106 and/or the application provider device 108.

The treatment management device 106 may be in communication directly (e.g., through local storage) and/or through the network 104 (e.g., in a cloud configuration or software as a service) with a database 110. The database 110 may store treatment regimen data 112 and electronic prescription data 114.

In some embodiments, the treatment regimen data 112 includes information regarding treatment regimens for diseases or ailments. A single treatment regimen or multiple treatment regimens may be included for a disease or ailment. The treatment regimen data may be included for a single disease or ailment or multiple disease or ailments. Examples of the treatment regimen data 112 may include treatment regimens for diseases or ailments such as hepatitis C, HIV, organ transplant, Multiple Sclerosis, Rheumatoid Arthritis, or other diseases or ailments that may have established general treatment regimens or protocols. Such treatment regimens may be relatively complex, for example including multiple different treatment components that may be taken concurrently and/or sequentially.

The electronic prescription data 114 includes information regarding electronic prescriptions that may be issued by medical professions on behalf of patients, for example to be filled by a pharmacy. Examples of the electronic prescription data 114 include patient names, medication or treatment (such as lab tests), dosing information, and the like.

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106, 108 or in parallel to link the devices 102, 106, 108.

In some embodiments, at least some of the functionality of the application provider device 108 may be included in the treatment management device 106. In such embodiments, the application may be downloadable directly from the treatment management device 106 or at direction of the treatment management device 106 from the database 110, which may store the application.

Figure 2:
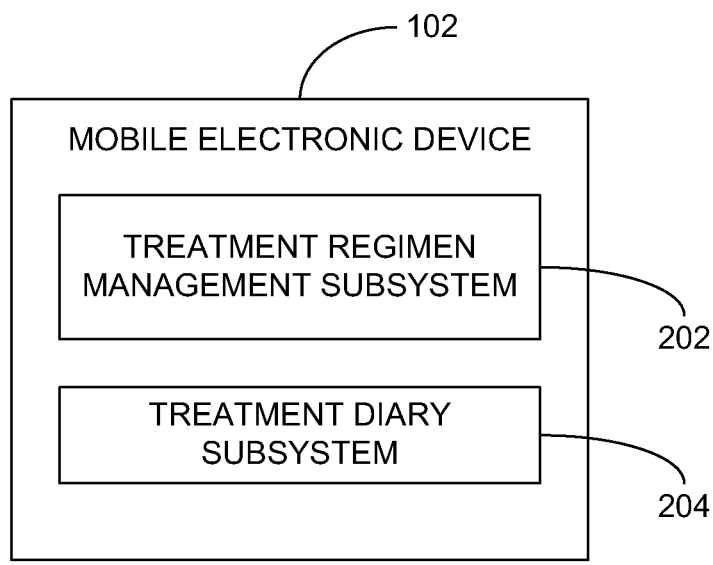
FIG. 2 is a block diagram of an example mobile electronic device that may be deployed within the system of FIG. 1, according to an example embodiment.

FIG. 2 illustrates the mobile electronic device 102, according to an example embodiment. The mobile electronic device 102 may be used by a device operator to manage a treatment regimen that the patient, who may include the device operator, is undergoing. The mobile electronic device 102 may be deployed in the system 100, or may otherwise be used.

The mobile electronic device 102 may include a treatment regimen management subsystem 202, and a treatment diary subsystem 204. While the various subsystems will be described as discrete subsystems for the purpose of explanation, the various functions of the subsystems may overlap with one another, and/or be performed, at least in part, by another of the subsystems. For the purpose of description, the subsystems and modules of the treatment regimen management subsystem 202 may be described as being embodied within the treatment management app. However, in some embodiments, one or more of the subsystems, modules, or both, may be fully, or partially, embodied in hardware, or may be fully, or partially, embodied in a separate application.

In general, the treatment regimen management subsystem 202 may allow the device operator to manage a treatment regimen to assist a patient, who may be the device operator or other individual, in undertaking the appropriate treatment at the appropriate time, according to a treatment schedule defined, at least in part, by the treatment regimen. For example, some treatment regimens may require multiple medications, or treatments such as lab tests, to be undertaken at designated times and/or on a continuous or regular basis over a defined period of time. Management of the treatment regimen may include, for example, identifying a treatment regimen associated with the patient, as well as scheduling and providing alerts corresponding to times at which a treatment should be undertaken.

Treatment diary subsystem 204 may enable the device operator to input and/or store information regarding aspects of the treatment regimen. Aspects of the treatment regimen may include, for example, information regarding compliance/noncompliance with the treatment regimen, side-effects of the treatment, and/or other information relevant to the treatment regimen. In some embodiments, the diary subsystem 204 may allow the device operator to input and/or store information in a free form format, responsive to specific questions, and/or a combination thereof. According to some embodiments, the treatment diary subsystem 204 may be capable of transmitting at least a portion of the treatment diary information, e.g., to a physician treating the patient, or to another third party. Transmission of treatment diary information may be controlled and/or configured by the device operator.

Figure 3:
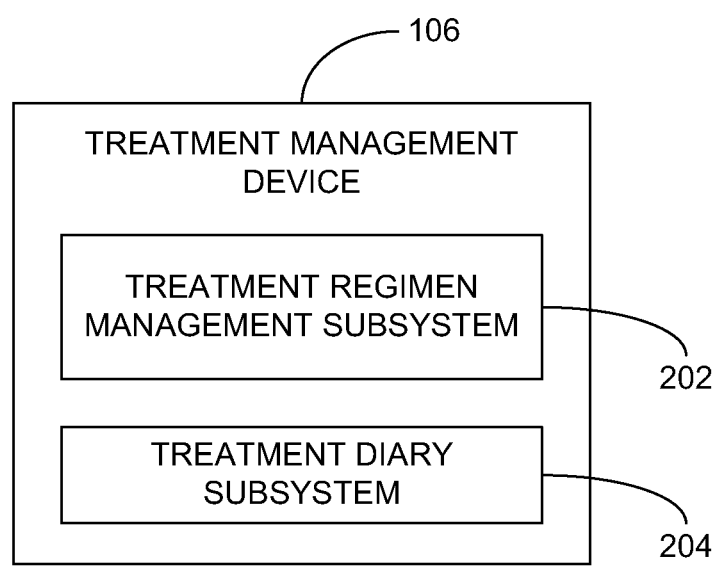
FIG. 3 is a block diagram of an example treatment management device that may be deployed within the system of FIG. 1, according to an example embodiment.

FIG. 3 illustrates the treatment management device 106, according to an example embodiment. The treatment management device 106 may be deployed in the system 100, or may be otherwise used.

The treatment management device 106 may include the treatment regimen management subsystem 202, and/or the treatment diary subsystem 204. In some embodiments one or more of the various subsystems 202-204 when used may provide server-side functionality to the mobile electronic device 102. By way of example, the treatment regimen management subsystem 202 may be deployed in both the mobile electronic device 102 and the treatment management device 106. The mobile electronic device 102 may then perform some of the functionality while other functionality is performed by the treatment management device 106.

Figure 4:
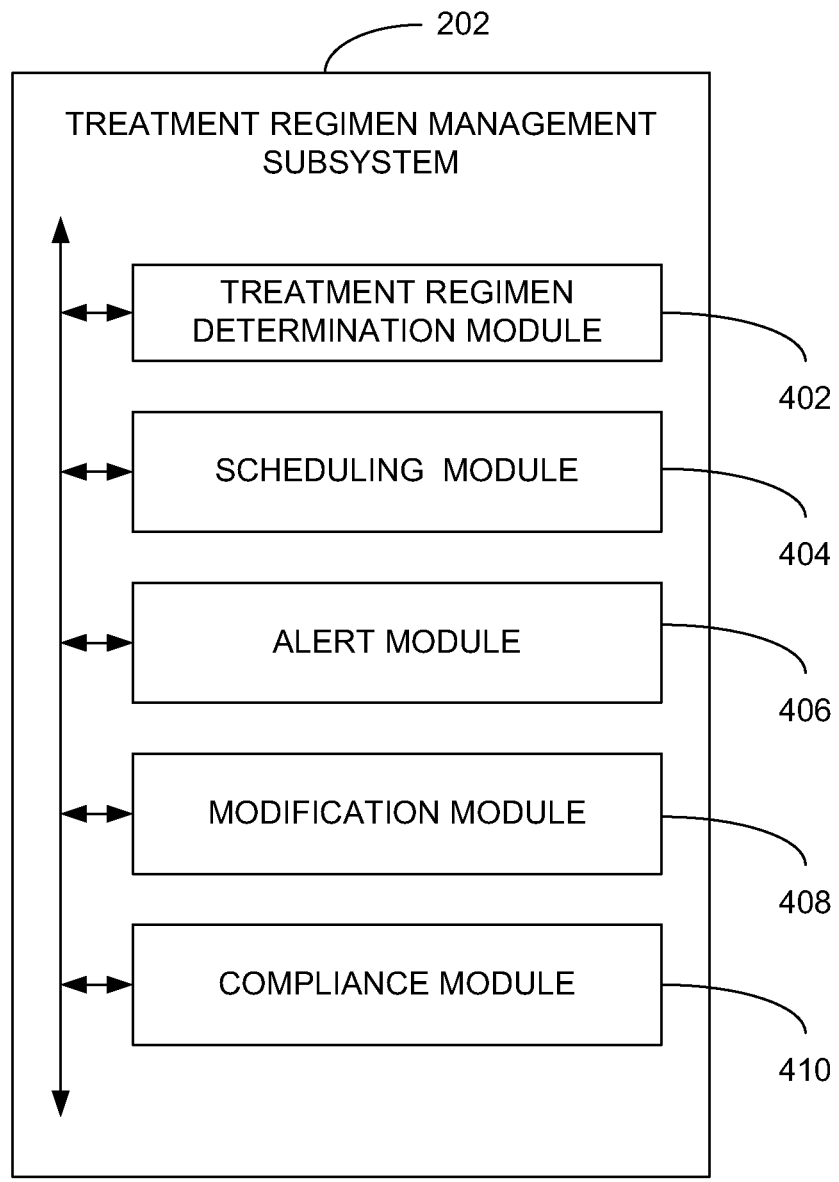
FIG. 4 is a block diagram of an example treatment regimen management subsystem that may be deployed within the mobile electronic device of FIG. 2 or the treatment management device of FIG. 3, according to an example embodiment.

FIG. 4 illustrates an example embodiment of the treatment regimen management subsystem 202 deployed in the mobile electronic device 102, the treatment management device 106, or otherwise deployed in another system, is shown including one or more modules communicatively coupled and included within the treatment regimen management subsystem 202 to enable the management of a treatment regimen of a patient by the device operator, who may, or may not, be the patient. Modules of the treatment regimen management subsystem 202 may include a treatment regimen determination module 402, a scheduling module 404, an alert module 406, a modification module 408, and a compliance module 410. One or more of the modules may be excluded, and/or two or more of the modules may be included as alternatives to one another. Other modules may also be included.

In some embodiments, the treatment regimen determination module 402 enables the device operator of the mobile electronic device 102 to identify a treatment regimen that has been prescribed for the device operator. The treatment regimen may, in some embodiments, include a systematic plan for the treatment, control, or management of a disease or ailment. In an example embodiment, the treatment regimen may include the use of a first treatment component and a second treatment component. In some embodiments, the treatment regimen may include one, or more than one, additional treatment components (e.g., a third treatment component, etc.). The treatment components (i.e., the first treatment component and the second treatment component, as well as any additional treatment components that may be utilized in connection with the treatment regimen) may each include a particular medication, prescription or nonprescription drug, pharmaceutical, and/or one or more other courses of treatment or activities involved in the treatment regimen, for example lab work that may be recommended as part of the treatment regimen. Each of the treatment components may also include a dosage associated with each of the particular medications, prescription or nonprescription drugs, pharmaceuticals, a type of lab work recommended, or the like.

A first treatment schedule may be associated with the first treatment component and a second treatment schedule may be associated with the second treatment component. In an embodiment including one or more additional treatment components, one or more additional treatment schedules may be associated with the additional treatment components (e.g., a third treatment schedule may be associated with the third treatment component, etc.). The treatment schedule associated with each of the treatment components may include an interval, timing, or frequency associated with the treatment component, for example, twice daily, once a week, or the like. For example, in an illustrative embodiment, the treatment regimen may include three different medications, and/or treatments such as lab work, and/or one or more medications to be taken in different dosages as different times. Each of the medications and/or treatments may have an associated treatment schedule. For example, a first medication may be prescribed at a given dosage to be taken twice daily. A second medication may be prescribed at a given dosage to be taken three times daily, and lab work may be recommended weekly.

In various embodiments, the treatment management app may be specific to the management of one specific disease or ailment, and/or the treatment management app may be capable of managing the treatment of various diseases or ailments. In embodiments in which the treatment management app may be capable of managing the treatment of various diseases or ailments, the treatment regimen determination module 402 may receive an indication of the disease or ailment being treated. For example, the treatment regimen determination module 402, and/or another subsystem or module of the treatment management app, may prompt (via a display device associated with the mobile electronic device 102) the device operator to input (via a user interface associated with the mobile electronic device 102) the disease or ailment to be treated. For example, the treatment regimen determination module 402 may receive a direct input of the disease or ailment and/or may receive a selection from a provided list of diseases or ailments.

As discussed above, in an embodiment the treatment regimen includes two or more treatment components, which each identify the medications or other treatments involved in the treatment regimen, as well as corresponding dosages or attributes of the medications or other treatments. The treatment regimen also identifies a treatment schedule associated with each of the treatment components. The treatment schedule associated with each of the treatment identifications may indicate the timing and/or frequency with which the treatment of the treatment component should be undertaken.

Further, and as generally discussed above, the treatment regimen may include a multi-component treatment regimen. For example, the treatment regimen may include a multi-dose treatment regimen in which the patient may undertake a treatment at varying dose, such as treatment quantity and/or treatment frequency, over time. In other examples, a multi-component treatment regimen may include a multi-modal treatment regimen, for example including a combination of injections, oral/topical medications, and/or recommended lab tests. In still other examples, a multi-component treatment regimen may include multi-dose and multi-modal treatment. Further, a multi-component treatment regimen may include a combination of any of the foregoing examples. Additionally, depending upon the nature of the disease or ailment, the treatment regimen may change over time. For example, the treatment regimen may include multiple discrete segments, in which each segment may have one or more treatment components and/or treatment schedules.

Some diseases or ailments may be treated by one of several generally defined protocols. Each protocol may include two or more medications or treatment procedures having associated treatment schedules. The medications or treatment procedures, as well as the associated treatment schedules, may be defined by the protocol. Determination of the treatment regimen may, in some embodiments, be made by the treatment regimen determination module 402. In some embodiments the treatment regimen determination module 402 may receive a selection of the treatment regimen from one or more available treatment regimens, which may, for example, correspond to one of the established treatment protocols for the disease or ailment. The available treatments may be, for example, preloaded on the mobile electronic device 102 as part of the treatment management app, or otherwise downloaded to the mobile electronic device 102 to enable the device operator to make a selection from one or more available treatment regimens. For example, the treatment regimen determination module 402 may provide, via a display associated with the mobile electronic device 102, a list of available treatment regimens stored on the mobile electronic device 102. The device operator may select, using a device user interface associated with the mobile electronic device 102, a treatment regimen from the list of available treatment regimens that corresponds to a treatment regimen prescribed to the device operator.

In some embodiments, the treatment regimen determination module 402 may determine the treatment regimen by accessing the database 110 including treatment regimen data 112. In such an embodiment, the treatment regimen determination module 402 may receive a user input indicative of the treatment regimen. Further, the treatment regimen determination module 402 may query the database 110 including treatment regimen data 112 (either directly or via the treatment management device 106) for the treatment regimen based upon, at least in part, the user input. For example, the treatment regimen determination module 402 may receive an input (via a user interface associated with the mobile electronic device 102) from the device operator identifying one or more aspects of the treatment regimen. Examples of aspects of the treatment regimen may include one or more medications included in the treatment regimen, the device operator's treatment history, one or more attributes of the device operator, or the like. The treatment regimen determination module 402 may receive the inputs as selections from provided lists of treatment regimen aspects, as inputs into specified fields, or otherwise.

The treatment regimen determination module 402 may issue a query to the database 110 including treatment regimen data 112 and/or to a database manager associated with the database 110 based upon the received user input. The query of the database 110 may return results including one, or multiple treatment regimens based upon the user inputs. The results may be transmitted to, and received by, the treatment regimen determination module 402. In some embodiments, the returned treatment regimen(s) may be presented to the device operator (e.g., via a display device associated with the mobile electronic device 102) for confirmation that the returned treatment regimen matches the treatment regimen prescribed for the device operator, or for a selection by the device operator indicating which one of the returned treatment regimens matches the treatment regimen prescribed for the device operator.

In some embodiments, the treatment regimen may be received by the mobile electronic device 102 from the database 110 including electronic prescription data 114, either directly or via the treatment management device 106. For example, the treatment regimen determination module 402 may query (via the mobile electronic device 102) the database 110 including electronic prescription data 114 relative to the identity, and/or an identifier of, the device operator and relative to one or treatments for the previously identified disease or ailment that have been prescribed to the device operator. The database 110 including electronic prescription data 114 may be a database associated with an electronic prescription system, such as that provided by SureScripts-RxHub, LLC.

In some embodiments, the treatment regimen determination module 402 may receive the exact treatment regimen for the device operator. In other embodiments, the treatment regimen determination module 402 may receive an indication of one or more prescribed treatments consistent with a treatment regimen. In such an embodiment, the one or more prescribed treatments may be compared, either by the mobile electronic device 102 or the treatment management device 106, to multiple possible treatment regimens to identify a correlation between the prescribed treatments and one or more possible treatment regimens. In the event that more than one possible treatment regimen is identified, the device operator may select (e.g., via a user interface associated with the mobile electronic device) a correct treatment regimen from the more than one possible treatment regimens.

The scheduling module 404 may communicate with an electronic calendar, for example a calendar application, to schedule treatment events within the electronic calendar. The calendar application may include calendar application functionality within the treatment management app, may be a separate calendar application executed by the mobile electronic device 102, and/or may be a calendar application that is accessible by the mobile electronic device 102 and/or the treatment management app, for example via network 104. An example of a calendar application that is accessible by the mobile electronic device 102 and/or the treatment management app may include GOOGLE Calendar by Google Inc. Each treatment event scheduled by the scheduling module 404 may include a particular treatment instance consistent with a treatment schedule associated with a treatment component, as determined by the treatment regimen determination module 402. For example, in an illustrative embodiment in which one treatment component includes a medication to be taken twice daily, two treatment events may be scheduled by the scheduling module 404 each day, in which one treatment event corresponds to each of the two times the medication is to be taken each day. In the event of a treatment regimen including multiple treatment components (e.g., medications and/or other treatments), the scheduling module 404 may schedule treatment events corresponding to each treatment component according to the treatment schedule associated with each treatment component.

Treatment events are generally individual administrations of a treatment component consistent with the treatment regimen and according to the treatment schedule associated with the treatment component. For example, in the illustrative example of an oral medication to be taken twice daily (e.g., BID), each of the twice daily administrations of the oral medication may be a treatment event. Further, in the illustrative example of two medications to be taken twice daily at the same time, each of the twice daily administrations of each of the two medications may be an individual treatment event, giving rise to four individual treatment events per day. In some embodiments, multiple treatment events taking place at the same time may be combined into a compound treatment event, for example that may be scheduled as a single treatment event including multiple parts. In the example of a compound treatment event, the multiple parts of the compound treatment event may correspond to each of the individual treatment events occurring at the same time.

The treatment events based upon each of the treatment schedules associated with each of the treatment components may be scheduled by the scheduling module 404. The scheduling module 404 may schedule the treatment events by interacting with a calendar application to create a calendar item corresponding to each treatment event based upon, at least in part, the treatment schedules of the treatment regimen. The calendar application may include integrated features of the treatment management application, may include a calendar application executed by the mobile electronic device 102, or may include a calendar application executed by another device accessible by, or capable of communicating with, the mobile electronic device. In an embodiment in which the calendar application is a feature of the treatment management application, the calendar interface module may directly communicate with the calendar application. In an embodiment in which the calendar application is a separate calendar application executed by the mobile computing device 102, the scheduling module 404 may schedule the treatment events via appropriate application programming interfaces (API's). Further, in an embodiment in which the calendar application is executed by a separate system, the scheduling module 404 may schedule treatment events via appropriate API's, web services calls, or other suitable communication mechanism.

Scheduling the treatment event may include receiving, in some embodiments, by the scheduling module 404 an indication of a preferred treatment time. In various example embodiments, the preferred treatment time may be a preferred treatment of the patient, a preferred treatment time of the caregiver, such as physician, or a preferred time based upon the treatment component (e.g., a medication that should be taken with a meal, etc.). The preferred treatment time may include, for example, a day of the week for receiving a once-weekly treatment. In other examples, the preferred treatment time may include preferred treatment times for once daily treatments, twice daily treatments, etc. In some embodiments, in response to receiving the indication of a preferred treatment time, the scheduling module 404 may modify default treatment time values. For example, a twice daily dosing (e.g., BID dosing) may have default treatment times of 9:00 AM and 6:00 PM. The scheduling module 404 may receive an indication of 10:00 AM and 7:00 PM as preferred treatment times of the patient. The treatment regimen management subsystem 202, and/or a module thereof, may schedule treatment events for twice daily treatments based upon, at least in part, the received preferred treatment times. In some embodiments, modification of the default treatment times may be constrained by treatment timing requirements associated with the medications, or other treatments, of one or more treatment events.

Conflicts arising between a scheduled treatment event and another event, such as a meeting or the like, may be resolved by the scheduling module 404. For example, a conflict may arise as a result of a treatment event being scheduled at the same time as another event that is scheduled via the calendar application. Further, the conflict may arise at the time that the treatment event is scheduled, or the conflict may arise when the other event is scheduled, subsequent to the treatment event being scheduled. According to an embodiment, the scheduling module may prompt the device operator to resolve the conflict by rescheduling the treatment event and/or by rescheduling the other event, such that the conflict is eliminated. In another embodiment, scheduling module 404 may allow the treatment event to be scheduled as a free event that may be scheduled in conflict with another event. In such an embodiment, the treatment event may be scheduled in conflict with another event, but may still be scheduled within the calendar application.

The alert module 406 may enable a treatment alert to be generated associated with one or more of the treatment events scheduled by the scheduling module 404 to therefore alert the device operator that a treatment is to occur. In various illustrative embodiments, the alert module 406 may provide instructions to a calendar application to generate an alert via the calendar application that is perceptible by the device operator. In other embodiments, the alert module 406 may provide instructions to the calendar application to generate a signal to the treatment management app indicating a treatment event. In such an embodiment, the treatment management app may generate an alert that is perceptible by the device operator.

In still further embodiments, the alert module 406 may provide instructions to the calendar application to generate an alert signal to another device, such as treatment management device 106, application provider device 108, or another external device that may provide a treatment event alert that is perceptible by the device operator, thereby alerting the device operator to the occurrence of the treatment event and/or an identification of the treatment to be undertaken by the device operator.

In some embodiments, the alert module 406 may generate a treatment alert in the form of a calendar reminder. For example, related to the scheduling of the treatment event in the calendar application, the alert module 406 may set an event characteristic of the scheduled treatment event to cause the calendar application to generate a reminder. The event characteristic may be set, for example, by direct communication between the alert module 406 and the calendar application, via an appropriate API, a web services call, or other suitable mechanism, as discussed above with respect to scheduling treatment events in the calendar application.

In some embodiments, the alert module 406 may generate a treatment alert in the form of an alert on a mobile device associated with the device operator of the mobile electronic device 102. The alert on the mobile device associated with the device operator may include an alert generated on the mobile electronic device 102. The alert may include, for example, an audio alert, a visual alert, such as a dialog box alert, or other alert perceptible by the device operator. In an embodiment, the calendar application may transmit an indication of the treatment event to the alert module 406. In response to receiving the indication of the treatment event, alert module 406 may generate an alert via the treatment management app, an operating system or user interface of the mobile electronic device 102, or another application executed on the mobile electronic device 102.

In some embodiments, the alert module 406 may generate an alert on a mobile device associated with the operator of the mobile electronic device 102 other than mobile electronic device 102, for example, a cellular telephone, a tablet computer, a netbook, etc. In a similar manner as discussed above, upon the occurrence of a treatment event the calendar application may transmit an indication of the treatment event to the alert module 406. In response to receiving the indication of the treatment event the alert module 406 may transmit an alert, or an instruction to generate an alert, to the mobile device. The alert, or the instruction to generate the alert may be transmitted via a suitable mechanism, such as a BLUETOOTH transmission, or a WiFi transmission. The mobile device upon which the alert is to be generated and/or the mechanism for transmitting the alert may be specified by the operator of the mobile electronic device 102, for example as a preference setting, or the like.

In some embodiments, the alert module 406 may generate a treatment alert in the form of a text message sent to a mobile device associated with the operator of the mobile electronic device 102. The mobile device associated with the operator may include the mobile electronic device 102 and/or may include another mobile device, such as a cellular telephone, associated with the operator of the mobile electronic device 102. For example, upon the occurrence of a treatment event the calendar application may transmit an indication of the treatment event to the alert module 406. In response to receiving the indication of the treatment event the alert module 406 may communicate with a text messaging application of the mobile electronic device 102, for example, via an appropriate API. In an embodiment in which the text message alert is to be transmitted to the mobile electronic device 102, the alert module 406 may transmit instructions to the text messaging application to generate an indication of a new received text message including an indicator of the treatment event. In an embodiment in which the text message alert is to be sent to a mobile device other than the mobile electronic device 102, the alert module 406 may transmit instructions to the text messaging application to generate an outgoing text message, including the indicator of the treatment event, to a specified recipient telephone number. The recipient telephone number may include a telephone number that was entered as an alert recipient preference of the treatment management app by the device operator of mobile electronic device 102. As such, a text message alert of the treatment event may be sent to a mobile device other than the mobile electronic device 102.

The modification module 408 may enable the device operator to modify one or more aspect of the treatment regimen determined by the treatment regimen determination module 402. For example, modification module 408 may enable the device operator to choose, or change, a timing of a treatment, change a dosage of a treatment, or otherwise modify the treatment regimen. Further, the scheduling module 404 and/or the alert module 406 may schedule treatment events and/or generate treatment alerts based upon, at least in part, the modified treatment regimen.

The compliance module 410 may receive an indication from the device operator that a treatment associated with a scheduled treatment event has been performed. The compliance module 410 may, thereby, record and track the degree of compliance of the device operator to the treatment regimen. The compliance module 410 may generate an intervention and/or warning message in the event of a detected noncompliance with the treatment regimen and/or treatment schedule. The noncompliance with the treatment regimen may be based upon, at least in part, a failure of the device operator to input an indicator of compliance. The intervention and/or warning message may include any variety of warning regarding consequences associated with noncompliance, inquiry messages regarding the reasons for noncompliance, and/or additional treatment alerts.

Figure 5:
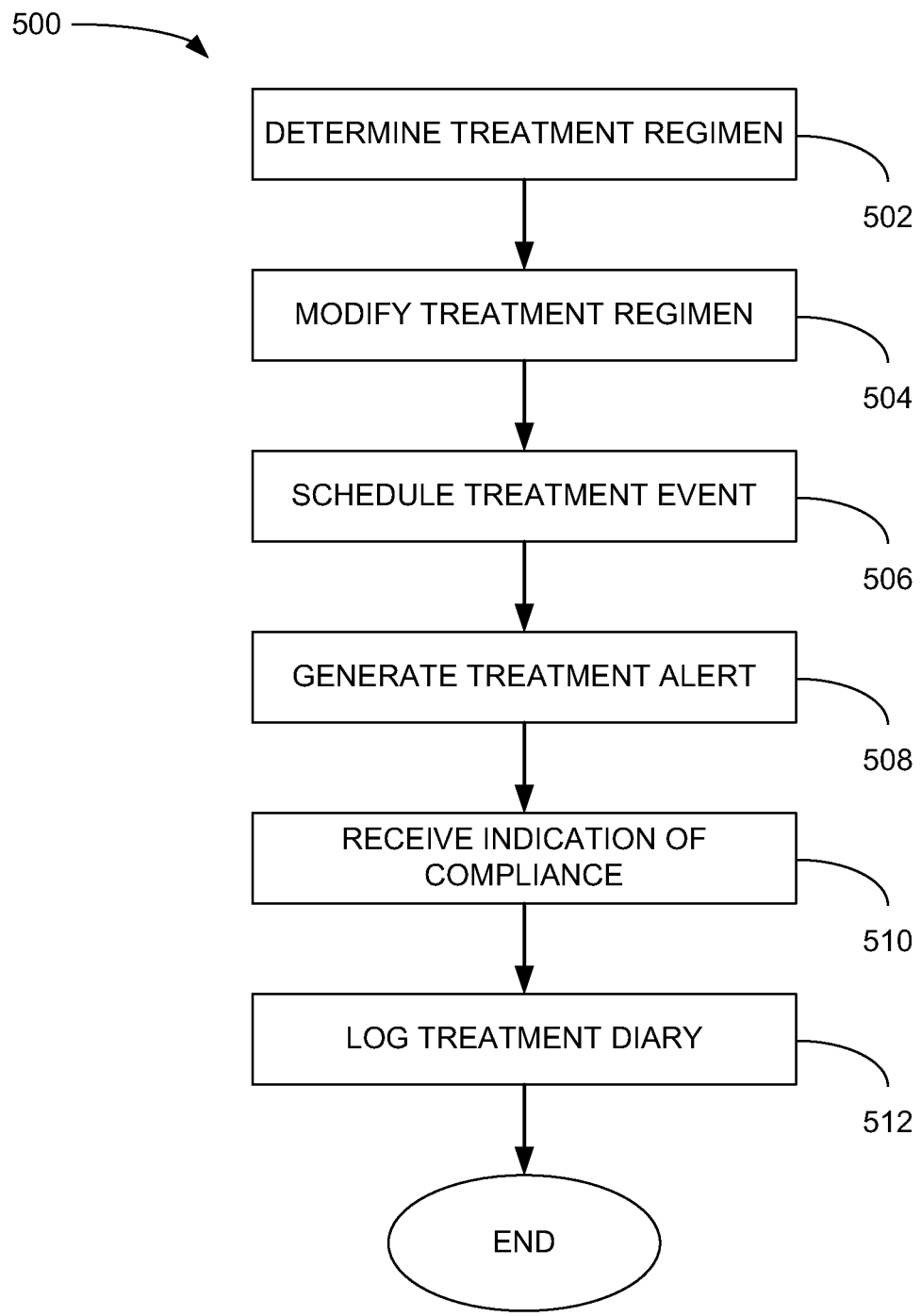
FIG. 5 is a block diagram of a flowchart illustrating a method for treatment regimen management, according to an example embodiment.

FIG. 5 illustrates a method 500 for treatment regimen management according to an example embodiment. The method 500 may be performed by the mobile electronic device 102, partially by the mobile electronic device 102 and partially by the treatment management device 106, or may be otherwise performed.

A treatment regimen for a patient undergoing treatment is determined at block 502. The treatment regimen for the patient may include a first treatment component and a second treatment component, and a first treatment schedule associated with the first treatment component, and a second treatment schedule associated with the second treatment component. Additional treatment components (e.g., a third treatment component, etc.) and additional treatment schedules (e.g., a third treatment schedule associated with the third treatment component, etc.) may also be included. Each of the treatment components may include a particular treatment, such as a medication, a treatment procedure such as a lab test to be performed, or other treatment, as well as any dosing of medication, type of lab test to be performed, or other characteristic of a treatment. Each of the treatment schedules may include a frequency and/or timing with which the treatment with an associated treatment component should occur. For example, an oral medication may have a treatment schedule of twice daily (e.g., BID) for a period of four weeks. In a similar example, lab testing to determine the patient's white blood cell count may have a treatment schedule of once a week for a period of six weeks.

In an embodiment, determining the treatment regimen may include receiving a selection of the treatment regimen from one or more available treatment regimens. For example, a given disease or ailment may have multiple possible treatment regimens. The device operator of the mobile electronic device 102 may be presented, via a visual display associated with the mobile electronic device 102, with a listing of possible treatment regimens. The device operator may select, using a selection device such as a touch screen associated with the mobile electronic device 102, the treatment regimen that has been prescribed for the patient (i.e., the device operator of the mobile electronic device 102).

In another embodiment, determining the treatment regimen may include receiving an input indicative of the treatment regimen and querying a treatment regimen database based upon, at least in part, the input. For example, the device operator may input, e.g., into an input field displayed on a display device associated with the mobile electronic device 102, one or more characteristics of the treatment regimen prescribed for the device operator. The characteristics of the treatment regimen may include a treatment, a treatment history, such as naive, treatment failure, a disease or personal characteristic of the patient, and/or other relevant information. The patient may be prompted for specific characteristics of the treatment regimen. Upon receiving the input from the device operator, a treatment regimen database, which may include various available treatment regimens for a given disease or ailment, may be queried for treatment regimens matching the input characteristics. The results of the query may be displayed via the mobile electronic device. The device operator may, in some embodiments, select the displayed treatment regimen as confirmation that it is the correct treatment regimen. In the event that more than one treatment regimen is returned based upon the query, the patient may select the one treatment regimen that corresponds to the treatment regimen prescribed for the patient.

In a further embodiment, determining the treatment regimen may include receiving an indication of a treatment regimen from an electronic prescription system. For example, if the prescriber of the treatment regimen utilizes an electronic prescription system, the electronic prescription system may be accessed relative to an identity of the patient. Depending upon the nature of the electronic prescription, the electronic prescription system may include the entire treatment regimen. In other embodiments, the treatment regimen may be determined based upon, at least in part, a comparison of prescribed treatments to a database including available treatment regimens for a given disease or ailment.

The treatment regimen may be modified at block 504. Modifying the treatment regimen may include modifying one or more of a treatment component and a treatment schedule of the determined treatment regimen. For example, a treatment regimen prescribed for a patient may vary in some manner from the determined treatment regimen. The patient may modify a treatment component and/or a treatment schedule associated with a treatment component of the determined treatment regimen, such that the modified treatment regimen corresponds to the prescribed treatment for the patient. The treatment regimen may be modified, for example, via the mobile electronic device 102 using any suitable input device associated with the mobile electronic device 102, such as a touch screen or other input device.

Treatment events are scheduled in a calendar application at block 506. The treatment events may include individual instances at which a treatment should occur based upon, at least in part, a treatment schedule associated with a treatment component. The calendar application may include a calendar feature that may be integrated into a treatment management app, which may in an embodiment implement the example method. In other embodiments, the calendar application may include a separate calendar application. Treatment events may be scheduled, for example, using appropriate API's allowing treatment events to be entered as calendar events in the calendar application. In a further embodiment, the calendar application may be executed by a separate device. For example, the calendar application may include a cloud-based calendar application. The treatment events may be scheduled in the cloud-based calendar application using web services interface, API's, and/or other suitable communication interfaces.

For example, in an embodiment including a multi-component treatment regimen, treatment events may be scheduled for each instance at which a treatment should occur for each treatment schedule associated with each treatment component. As an illustrative example of this scheduling, a treatment regimen may include a first treatment component including a once-weekly injection, a second treatment component including a twice-daily oral medication, and a third treatment component including a three-times daily oral medication. Consistent with this example, a series treatment events corresponding to the first treatment component (e.g., injection treatment events) may be scheduled at one week intervals. A series of treatment events corresponding to the second treatment component (e.g., first medication treatment events) may be scheduled twice daily, for example at 9:00 AM and 6:00 PM. Similarly, a series of treatment events corresponding to the third treatment component (e.g., second medication treatment events) may be scheduled three times daily, for example at 9:00 AM, 1:00 PM, and 6:00 PM. The day and timing of the treatment events may be based upon a default day/time and/or may be based upon a selection by the patient.

In an embodiment, scheduling the treatment events may include receiving an indication of a preferred treatment time. For example, and referring to the previous example including a three treatment component treatment regimen, a patient may prefer to take the morning dose of the first medication and the second medication at 8:00 AM. Using an appropriate user interface and input device, the patient may input the desired 8:00 AM timing for the morning treatment events into the mobile electronic device 102. Similar indications of preferred treatment times may be input for other treatment events.

To the extent that the treatment regimen may have been modified at block 504, scheduling the treatment events at block 506 may include scheduling treatment events based upon the modified treatment regimen.

Treatment alerts are generated at block 508. Treatment alerts may include any alert perceptible by the patient (e.g., as the device operator of the mobile electronic device 102) at the time of the scheduled treatment events in the calendar application. Treatment alerts at the time of the scheduled treatment events contemplates the generation of treatment alerts preceding the scheduled treatment event by a reminder period, and/or treatment alerts after the scheduled treatment event based upon, at least in part, a snooze functionality associated with the treatment alert, and/or a failure of patient to acknowledge the treatment alert.

In various embodiments, generating the treatment alert may include generating a calendar reminder, as may occur with other events scheduled in a calendar application, generating an alert on a mobile device associated with the patient, and transmitting a text message to a mobile device associated with the patient. Calendar reminders may, for example, be generated by providing instructions to the calendar application, e.g., during scheduling of a treatment event to provide a reminder of the event. Alerts may be generated on a mobile device associated with the patient by, for example, providing instructions for generating a treatment alert through an application executed on the mobile device (such as a treatment management app executed on the mobile electronic device 102) and/or for generating the treatment alert through an operating system or user interface feature of the mobile device. Further, generating the treatment alert on a mobile device associated with the patient may include sending instructions, for example, via a wireless communications channel, to another mobile device associated with the user, such as a cellular telephone, a tablet computer, or a netbook. Moreover, transmitting a text message to a mobile device associated with the user may include transmitting instructions to a text messaging application, for example via a suitable API, to transmit a text message to a telephone number indicated by the patient, e.g., as a preference or set-up parameter of a treatment management app.

An indication of compliance with the treatment schedule may be received at block 510. For example, attend to the occurrence of a treatment event, a compliance dialog box may be rendered on a display screen associated with the mobile electronic device 102 requesting that the patient indicate whether the scheduled treatment was undertaken. The patient may indicate whether the treatment was undertaken by selecting a "yes" or "no" check box within the dialog box, and/or via other suitable mechanism.

In some embodiments, in the event of a "no" response in the compliance dialog box, an intervention message may be generated. The intervention message may, for example, include information such as warnings of the risks associated with noncompliance, such as decreased treatment efficacy, or other suitable message. Additionally, in some embodiments an intervention message may request that the patient indicate, as by selecting one or more available options, the reason for noncompliance.

In various embodiments, compliance information (i.e., indications of complains or of noncompliance with the treatment schedule), and/or reasons for noncompliance may be transmitted to a storage system, such as a database, for statistical analysis. The compliance information may be de-identified (i.e., disassociated from the identity of the patient) and/or otherwise made Health Insurance Portability and Accountability Act (HIPAA) compliant.

In some embodiments, treatment diary information may be logged at block 512. For example, the patient may be enabled to enter information regarding treatment. Information regarding treatment may include, for example, experienced side effects, subjective feelings of well being, lab results, or other information that may be relevant to the treatment of the patient. The treatment diary information may be stored on the mobile electronic device 102 and/or may be transmitted to a storage system, such as a database. As with the compliance information, any treatment diary information may be de-identified and/or otherwise made HIPAA compliant.

FIGS. 6-13 are example displays 600-1300, according to example embodiments. The displays 600-1300 include example data and may be generated by one or more of the treatment regimen management subsystem, and the treatment diary subsystem and ultimately presented to an operator of the mobile electronic device. However other types of displays and modifications to the displays may additionally or alternatively be presented.

For the purpose of the following illustrative embodiment, displays are shown relative to the management of a treatment regimen for hepatitis C, in which the treatment regimen includes a multi-component treatment regimen including three treatment components, e.g., in the form of medications, and two modalities of treatment, namely an injectable medication and two oral medications. However, other treatment regimens including greater or fewer treatment components, greater or fewer numbers of treatment modalities, and/or other treatment types may be implemented in a similar manner. Additionally, while not shown in the illustrative examples below, additional displays, such as a sign-in display requiring a username and password, etc., may also be included.

Figure 6:
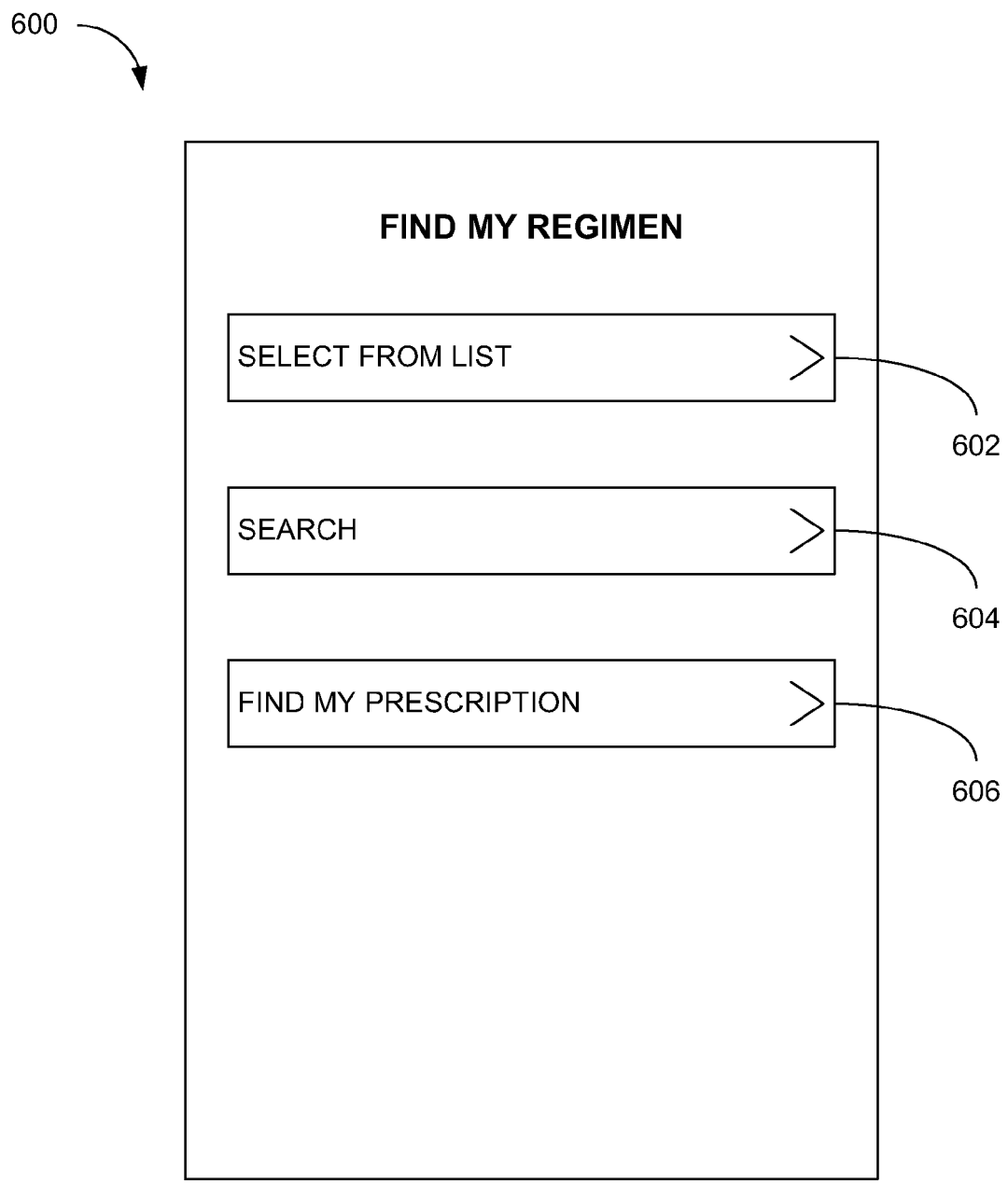
FIGS. 6-13 are example displays, according to example embodiments.

The display 600 of FIG. 6 is an example of a treatment regimen determination menu display that may be presented to the device operator of the mobile electronic device 102 when an application that incorporates at least a part of the functionality of the subsystem 202 (see FIG. 2) is launched. As shown in the display 600, the device operator is invited to select a method by which the device operator wishes their treatment regimen to be determined. The device operator is presented with a number of buttons 602, 604, 606 on the display 600. The buttons 602, 604, 606, when selected, may launch functionality for determining the treatment regimen of the device operator by enabling the device operator to select a treatment regimen from a list, by conducting a search for the treatment regimen of the device operator, or by accessing a prescription of the device operator associated with the treatment regimen. For example, selecting the select from list button 602 may enable the device operator to select a treatment regimen from a list of available treatment regimens, which may be preloaded and/or may be downloaded in response to the device operator selecting the select from list button 602. Selecting the search button 604 may enable to device operator to search for a treatment regimen, for example, based on one or more treatment components included in the treatment regimen, a patient status (e.g., treatment naïve, treatment failed), or other characteristic that may be indicative of a treatment regimen. Further, selecting the find my prescription button 606 may enable an electronic prescription system to be queried relative to a treatment regimen, for example, based on an explicitly prescribed treatment regiment, one or more prescribed treatments, or other information accessible from a database including electronic prescription data.

Figure 7:
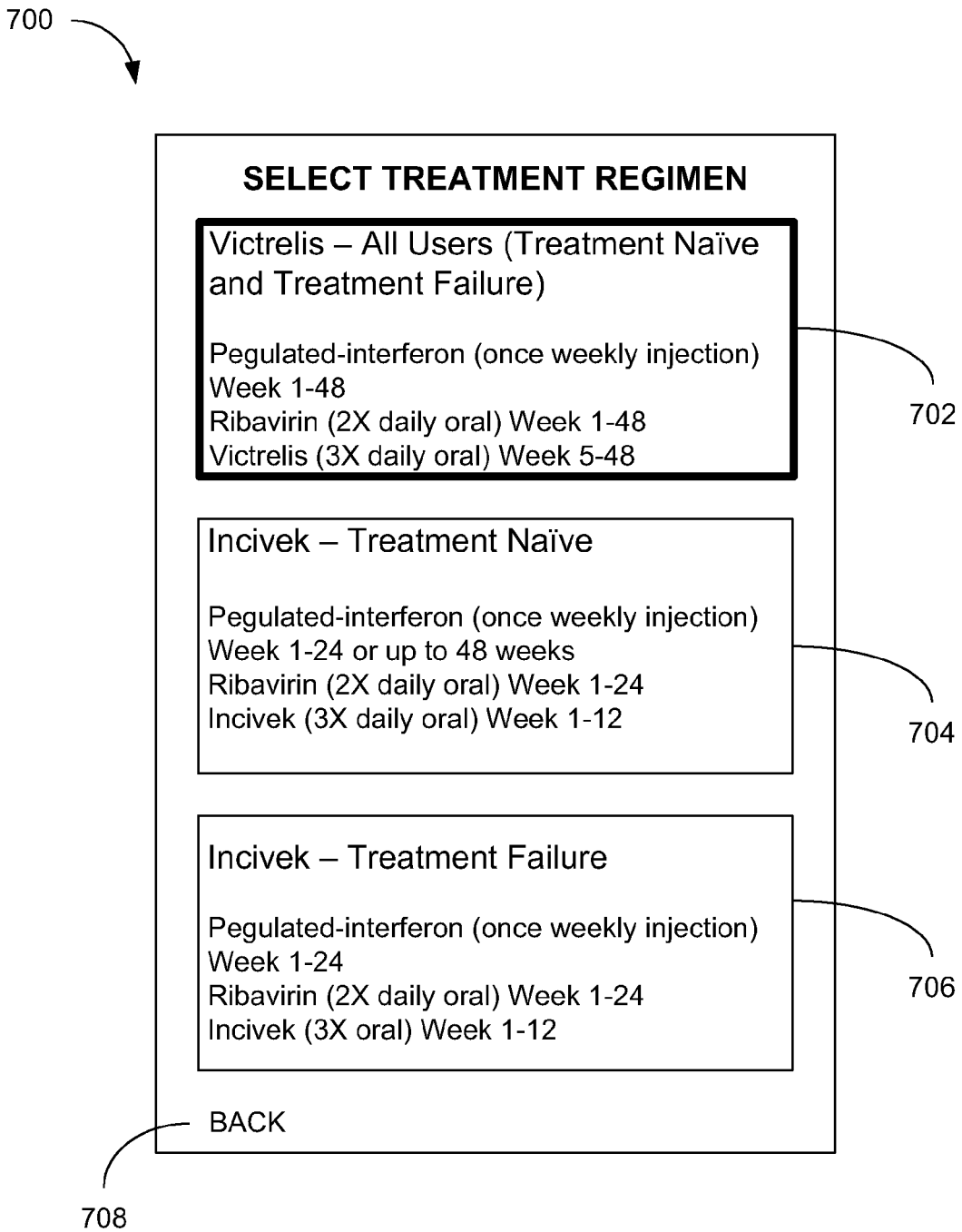
Figure 8:
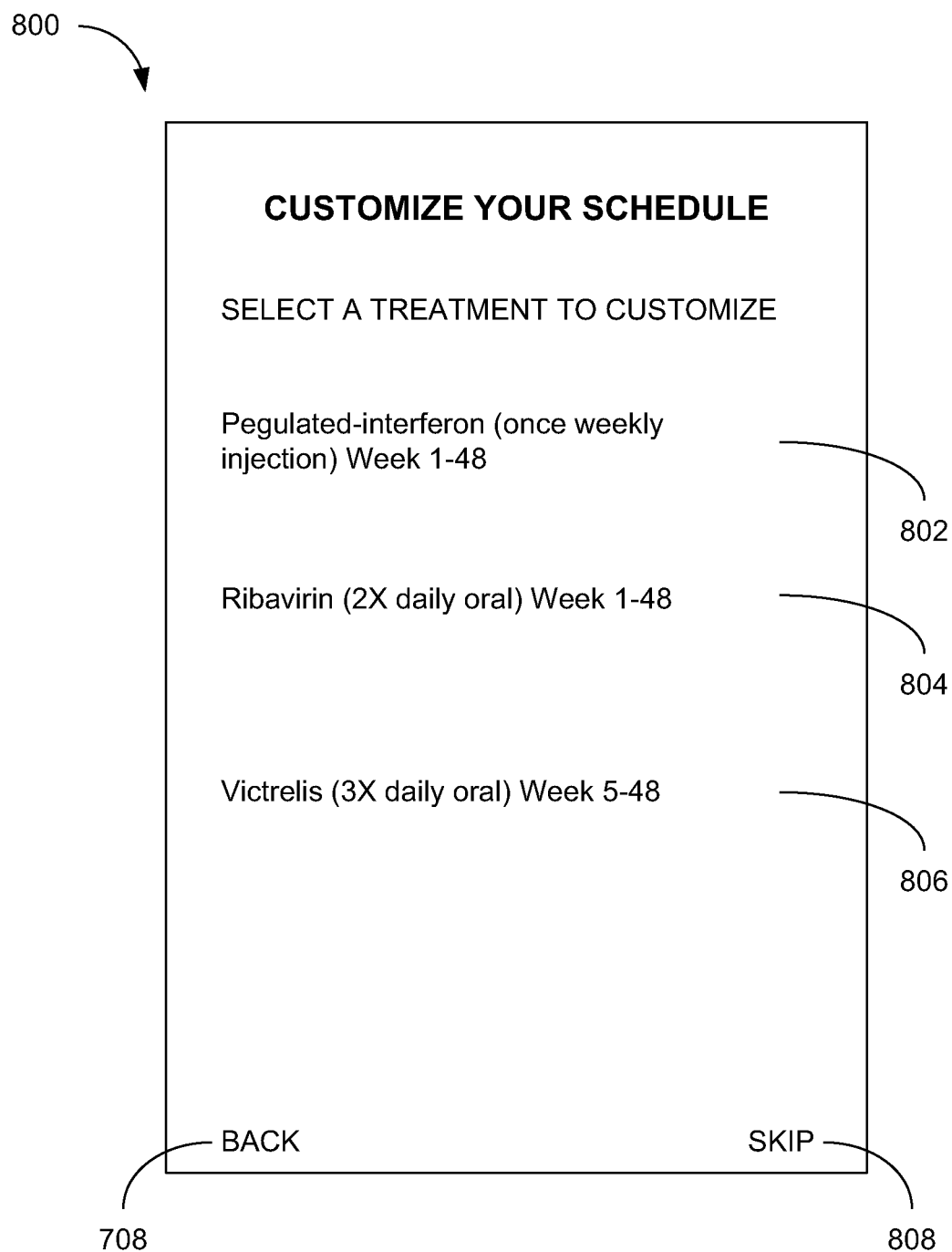

For the purpose of illustration, if the device operator selects the select from the list selection button 602 the display 700 of FIG. 7 may be presented to the device operator. The device operator may select the list selection button 702 using an appropriate input device, such as a touch screen display associated with the mobile electronic device 102. The display 700 may include a list of available treatment regimens for hepatitis C 702, 704, 706. The device operator may select one of the listed available treatment regimens 702, 704, 706 from display 700 that corresponds to the treatment regimen prescribed for the device operator. As shown, in some embodiments one of the available treatment regimens, for example the treatment regimen 702, may be selected by default. If the treatment regimen prescribed for the device operator is not included on the display 600, the device operator may select the back selection 708 to return to the previous display 600 to select a different method for determining the treatment regimen prescribed for the device operator.

If the device operator determines the treatment regimen 702, included in the display 700, is the treatment regimen prescribed for the device operator, the device operator may select the treatment regimen 702. If the device operator selects the treatment regimen 702, a display 800 of FIG. 8 may be presented to the device operator. The display 800 may present the device operator with options to customize the treatment schedule of the several treatment components included in the selected treatment regimen. As shown, the display 800 may include each of the treatment components included within the selected treatment regimen as a selectable treatment item 802, 804, 806. The device operator may choose to customize the treatment schedule of one of the treatment components by selecting one of the selectable treatment items 802, 804, 806. If the device operator does not wish to customize a treatment schedule of one of the treatment components of the selected treatment regimen, the device operator may select the skip selection 808 within the display 800 to move to the next display without customizing a treatment schedule.

Figure 9:
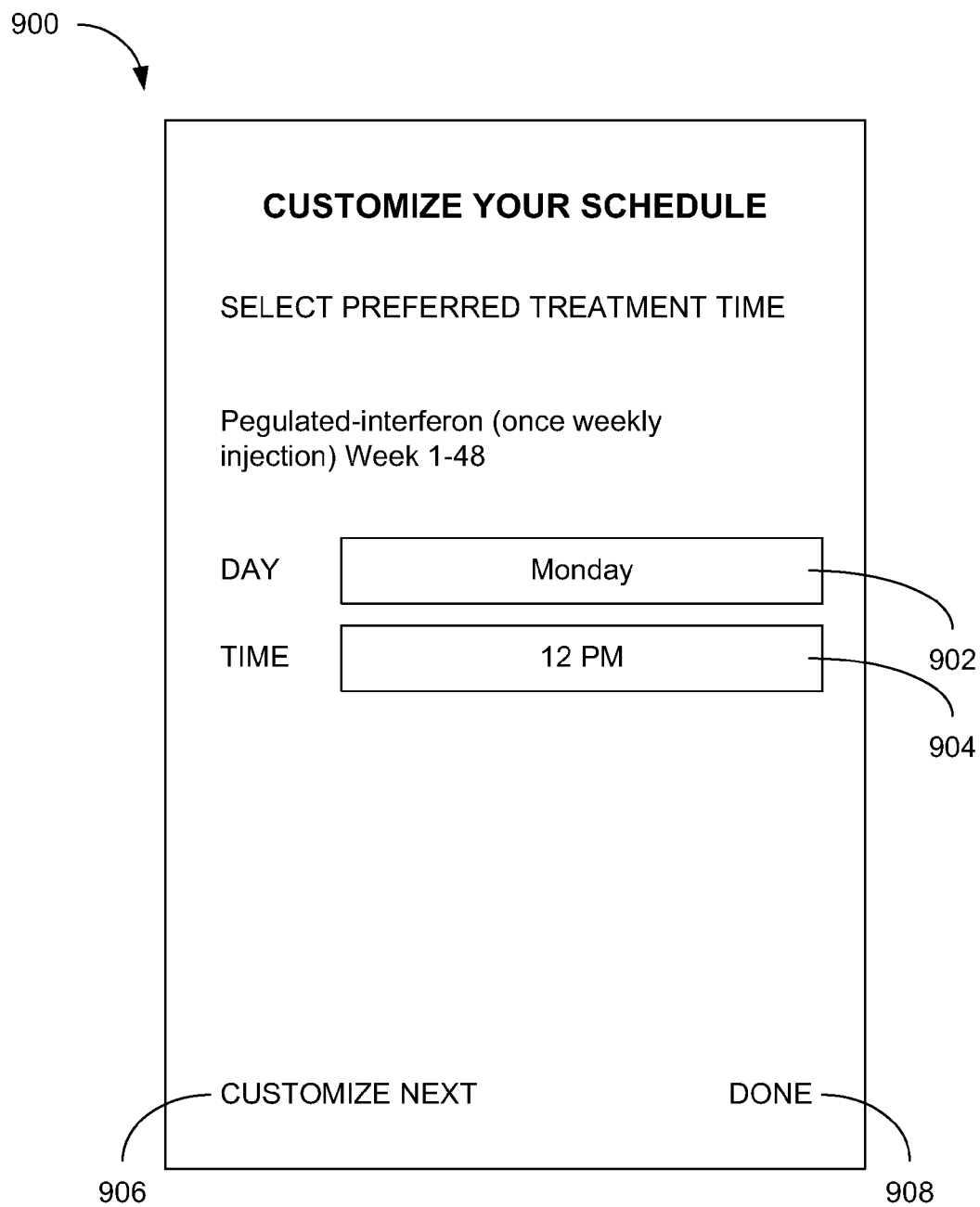
Figure 10:
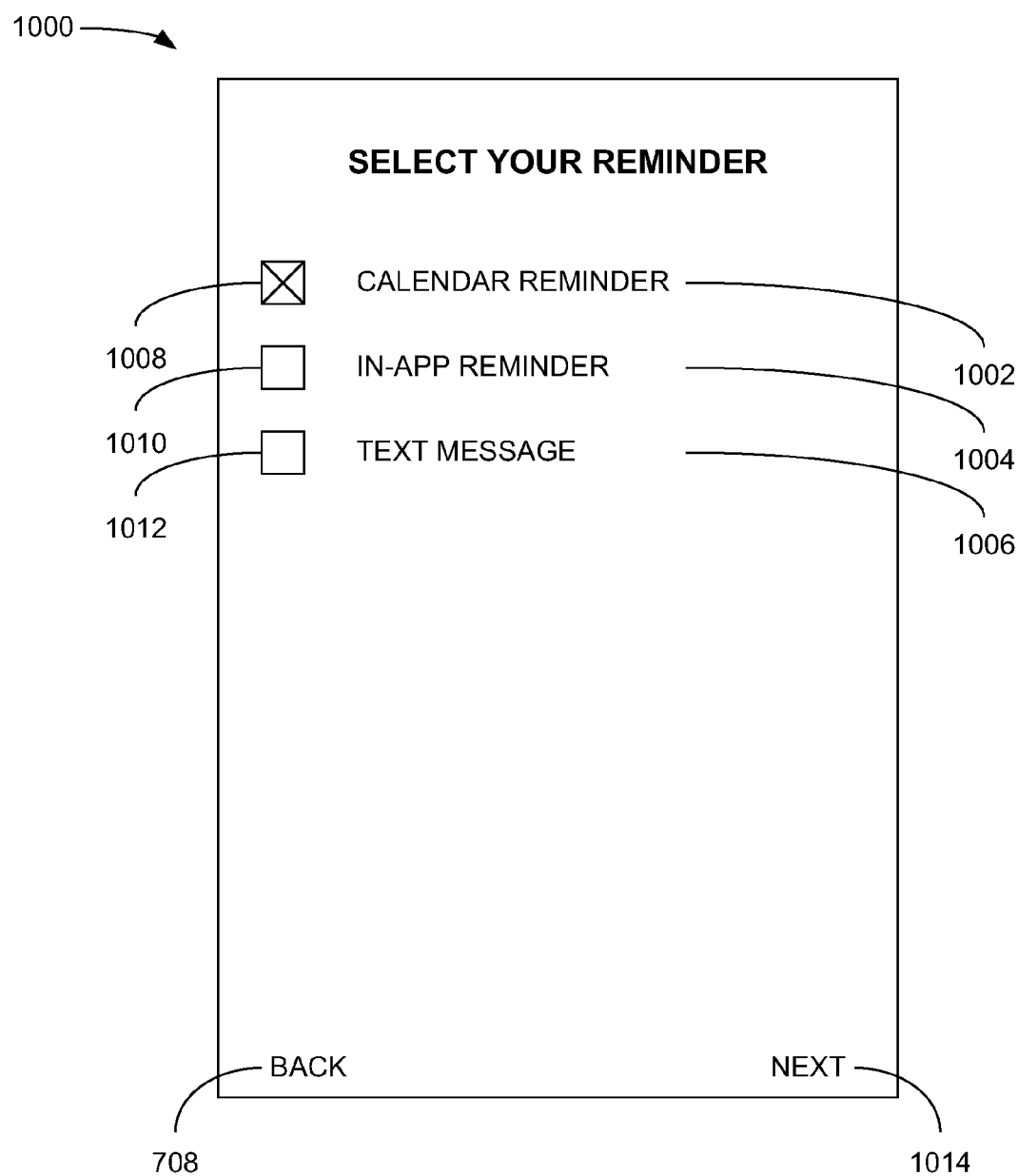
Figure 11:
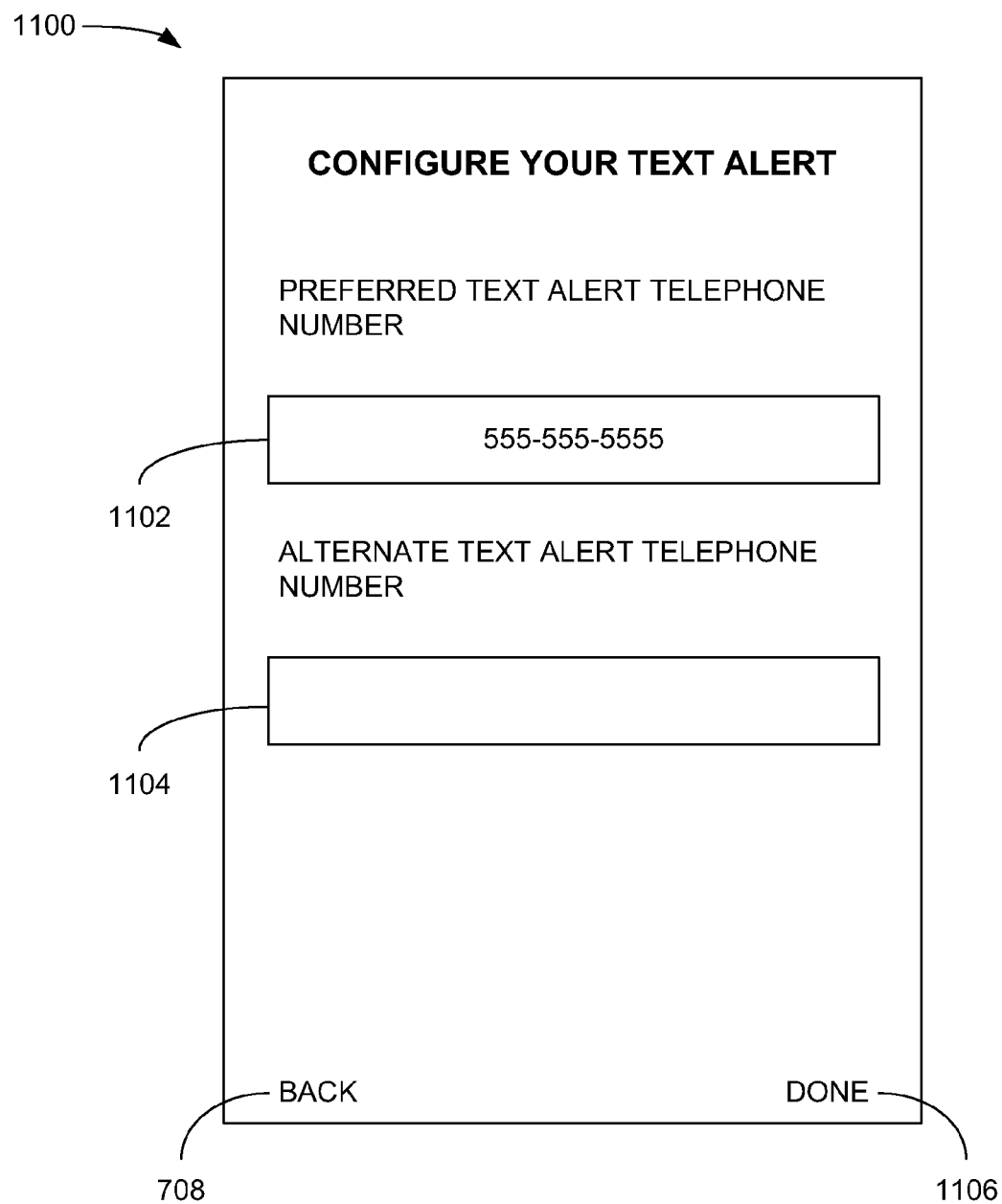

When the device operator selects one of the selectable treatment items 802, 804, 806, for example the selectable treatment item 802, the display 900 of FIG. 9 may be presented to the device operator. The display 900 may include day and time fields 902, 904 to enable selection of a preferred day and time for the selected treatment. The day and time fields 902, 904 may display default settings for day and time of the selected treatment. The device operator may customize the value in one, or both, of the day and time fields 902, 904 by selecting, one at a time, the day and time fields 902, 904 to modify the default value to a preferred value.

While not shown, upon selecting one of the day and time fields 902, 904 and additional display, such as a popup display or the like, may be presented to the device operator. The additional display may include fields, such as days and/or times, that may be selected to modify the default value included within the selected day or time field. Additionally, the display 900 includes the display field 902 including a preferred day and the display field 904 including a single time. The illustrated display fields 902, 904 are relevant to the selected treatment of Pegulated-interferon to be taken once weekly. The selection of other treatment components including different treatment schedules, for example twice daily, may include different input fields that may be relevant to the treatment schedule of such treatment. For example, in the example of a treatment component having a treatment schedule of twice daily, the display for inputting a preferred treatment time may include two time fields relevant to the twice daily treatment schedule.

The display 900 also includes a customize next selection 906. Selecting the customize next selection 906 may allow the device operator to input a preferred treatment time for another treatment component associated with the selected treatment regimen. In some embodiments, if the input preferred treatment time does not meet a verification criterion, which may be based on, for example, clinical information, a display informing the device operator that the input preferred treatment time does not comply with the treatment regimen may be provided. Inputting a preferred treatment time for another treatment component associated with the selected treatment regimen may be accomplished through a display similar to the display 900. Additionally, the display 900 may include a done selection 908. Upon completion of inputting a preferred treatment time, the device operator may select the done selection

908. When the device operator selects the done selection 908, the display 1000 of FIG. 10 may be presented to the device operator.

The display 1000 may include configuration options 1002, 1004, 1006 for configuring a desired treatment alert. The device operator may check one or more of the checkboxes 1008, 1010, 1012 to select a treatment alert method for alerting the device operator of a treatment event. In some embodiments, one or more of the checkboxes, for example checkbox 1008, may be selected by default. Such a default selection may be altered by the device operator, for example by unchecking the checkbox. Upon completion of selections, the device operator can proceed to the next display by selecting the next selection 1014 from within the display 1000.

By way of example, the device operator may check the checkbox 1012 indicating a desire to receive treatment alerts at least via text message. Upon selecting the next selection 1014, the display 1100 of FIG. 11 may be presented to the device operator. The display 1100 may include the input fields 1102, 1104 that may allow the device operator to input a telephone number to which a text message treatment alert may be transmitted. In an embodiment in which the mobile electronic device 102 includes a smart phone, or data enabled cellular telephone, the input field 1102 may include the telephone number of the mobile electronic device 102 as a default value. The device operator may change the default value in input field 1102.

In some embodiments, the device operator may input an additional telephone number in the input field 1104 to which a treatment alert text message should also be transmitted. In a similar manner as described above, upon selecting one of the input fields 1102, 1104, an additional display may be presented to the device operator, such as a numeric keypad via which the device operator may input a telephone number. Upon completing input of text alert telephone numbers the device operator may select the done selection 1106. Selecting the done selection 1106 may complete the user configuration of the treatment regimen management. Upon completing of the treatment management system one or more of the subsystems 202-204 may be execute to schedule treatment events within a calendar application and generate treatment alerts.

Figure 12:
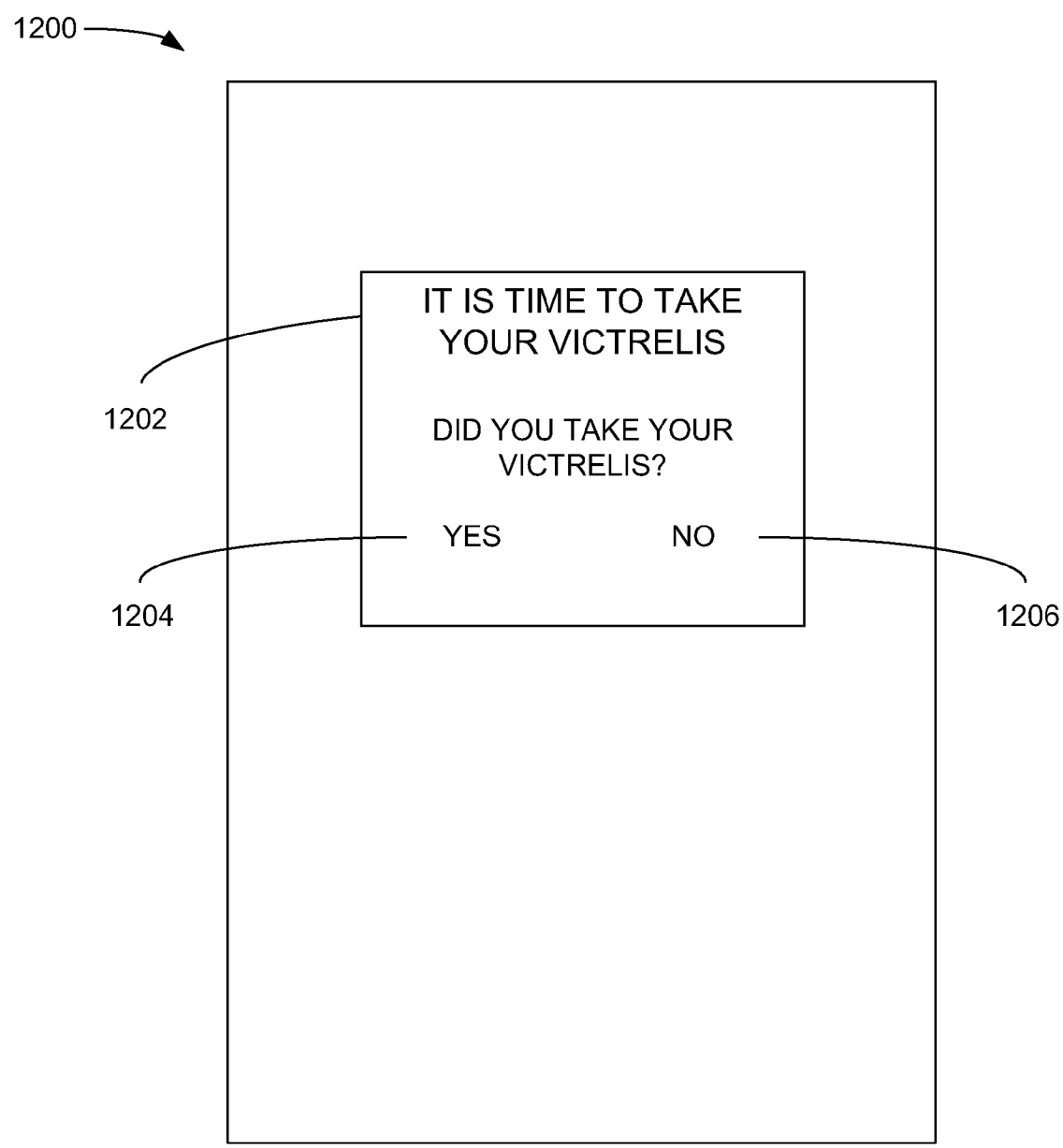

Referring to FIG. 12, upon the occurrence of a treatment alert the display 1200 may be presented to the device operator. Display 1204 may include an alert box 1202. The alert box 1202 may include a text indicator that it is time to undergo a treatment, for example taking the medication Victrelis in the illustrated example. Additionally, the display may include compliance features in the form of a selectable yes option 1204 and a selectable no option 1206, respectively associated with the compliance query did you take your Victrelis. The device operator may select the yes option 1204 or the no option 1206 according to whether the patient, who may or may not be the device operator, as discussed above, had taken the medication.

Figure 13:
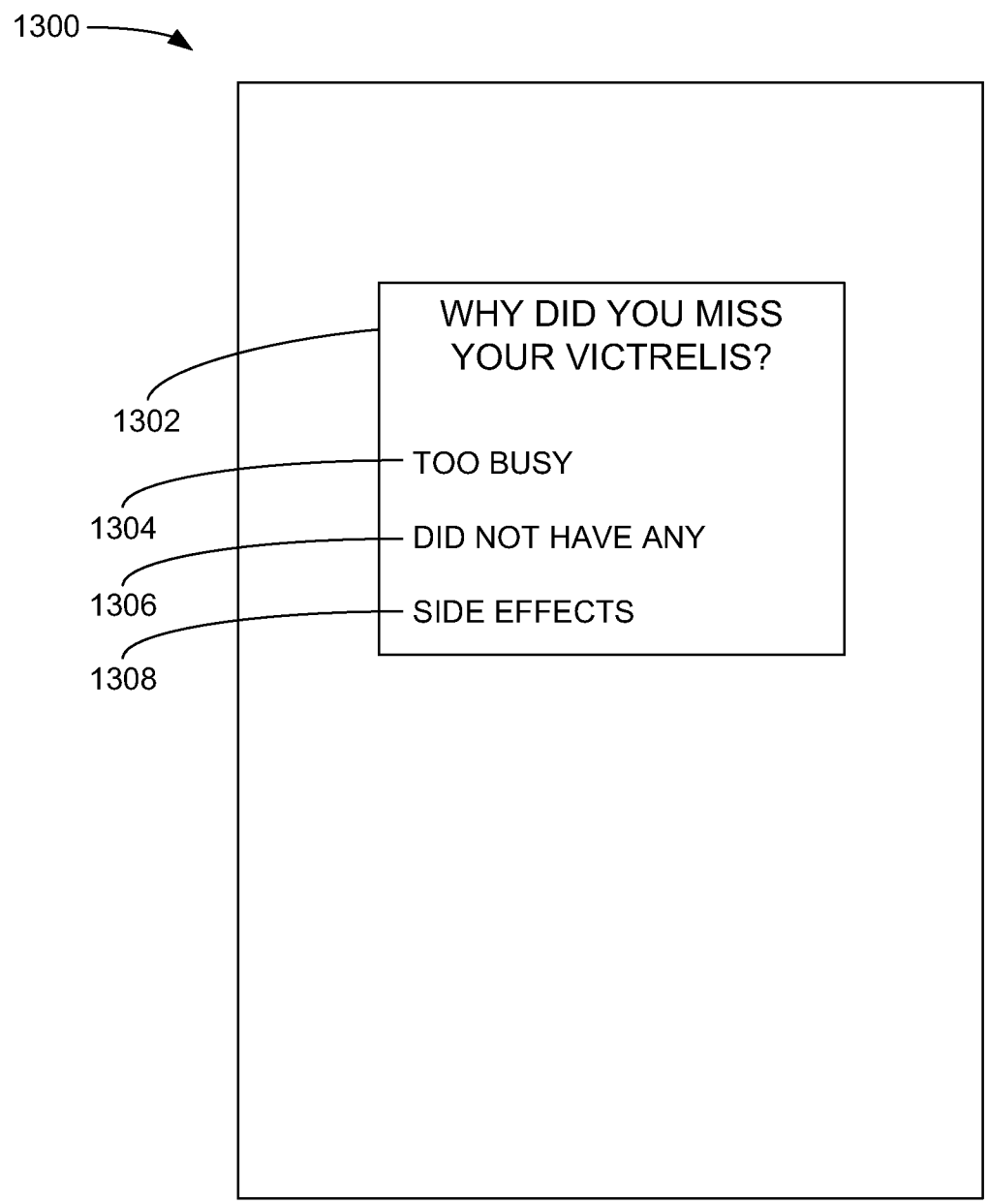

In the event that the device operator selects the no option 1206 associated with the compliance query, the display 1300 of FIG. 13 may be presented to the device operator. The display 1300 may include a noncompliance dialog box 1302. The noncompliance dialog box 1302 may include selectable noncompliance options 1304, 1306, 1308 that may be selected to explain why the device operator did not comply with the treatment schedule. While three noncompliance options are depicted, various additional and/or alternative noncompliance options may be displayed. Additionally, the noncompliance options may be selected via checkboxes, for example, which may allow the device operator to indicate more than one reason for noncompliance. Additionally, the noncompliance dialog box 1302 may include one or more intervention messages, such as a warning as to the possible ramifications of not complying with the treatment schedule.

While a number of different types of user interface elements have been reflected above, other types of user interface elements may be used to perform the same or similar functionality.

Figure 14:
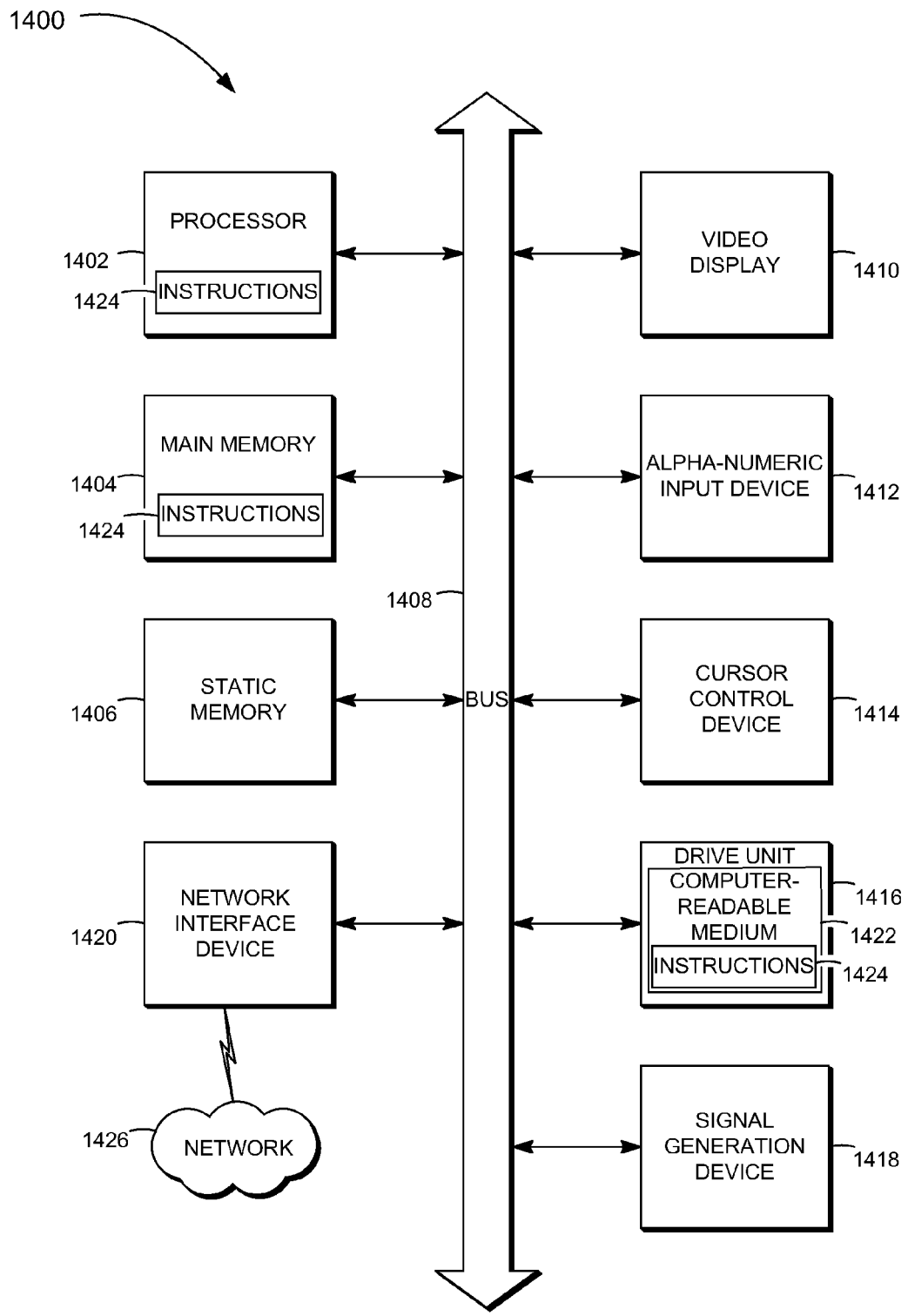
FIG. 14 is a block diagram of a machine in the example form of a computer system within which a set of instructions for causing the machine to perform any one or more of the methodologies discussed herein may be executed or stored.

FIG. 14 shows a block diagram of a machine in the example form of a computer system 1400 within which a set of instructions may be executed causing the machine to perform any one or more of the methods, processes, operations, or methodologies discussed herein. The mobile electronic device 102, the network manager device 106, and/or the application provider device 108 may include the functionality of the one or more computer systems 1400.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1400 includes a processor 1402 (e.g., a central processing unit (CPU) a graphics processing unit (GPU) or both), a main memory 1404 and a static memory 1406, which communicate with each other via a bus 1408. The computer system 1400 further includes a video display unit 1410 (e.g., a liquid crystal display (LCD) or a cathode ray tube (CRT)). The computer system 1400 also includes an alphanumeric input device 1412 (e.g., a keyboard), a cursor control device 1414 (e.g., a mouse), a drive unit 1416, a signal generation device 1418 (e.g., a speaker) and a network interface device 1420.

The drive unit 1416 includes a computer-readable medium 1422 on which is stored one or more sets of instructions (e.g., software 1424) embodying any one or more of the methodologies or functions described herein. The software 1424 may also reside, completely or at least partially, within the main memory 1404 and/or within the processor 1402 during execution thereof by the computer system 1400, the main memory 1404 and the processor 1402 also constituting computer-readable media.

The software 1424 may further be transmitted or received over a network 1426 via the network interface device 1420.

While the computer-readable medium 1422 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The terminology used herein is for the purpose of describing illustrative embodiments only and is not intended to be limiting of the invention. As used herein, the singular forms "a", "an" and "the" are intended to include the plural forms as well, unless the context clearly indicates otherwise. The term "based on" or using, as used herein, reflects an open-ended term that can reflect others elements beyond those explicitly recited. It will be further understood that the terms "comprises" and/or "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a treatment regimen associated with a patient may be determined. The treatment regimen may include a first treatment component and a second treatment component. A first treatment schedule may be associated with the first treatment component and a second treatment schedule may be associated with the second treatment component. Multiple treatment events may be scheduled in an electronic calendar. The treatment events may be based upon, at least in part, the first treatment schedule and the second treatment schedule associated with the first treatment component and the second treatment component. A treatment alert associated with each of the treatment events may be generated.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving, on a mobile device processor, a treatment regimen associated with a patient, the treatment regimen being associated with treatment of a particular health condition of the patient and including a first treatment component and a second treatment component, and a first treatment schedule associated with the first treatment component and a second treatment schedule associated with the second treatment component;

scheduling, on the mobile device processor, a plurality of treatment events in an electronic calendar, the plurality of treatment events scheduled to treat the particular health condition and based on the first treatment schedule and the second treatment schedule associated;

generating, on the mobile device processor, a plurality of patient treatment alerts, a patient treatment alert of the plurality of patient treatment alerts associated with a treatment event of the plurality of treatment events;

receiving, on the mobile device processor, a plurality of compliance indications associated with the first treatment schedule and the second treatment schedule from a mobile device operator;

determining, on the mobile device processor, noncompliance with the first treatment schedule, the second treatment schedule, or both the first treatment schedule and the second treatment schedule based on receipt of the plurality of compliance indications;

generating, on the mobile device processor, a patient intervention display on the mobile electronic device associated with treatment of the particular health condition in response to a determination of the noncompliance, the patient intervention display including a patient noncompliance query and a plurality of potential patient noncompliance indications, the plurality of potential patient noncompliance indications including a personal non-availability indication, a no prescription drug available indication, and a prescription drug side effects indication;

receiving, on the mobile device processor, a patient indication of noncompliance with the treatment regimen in response to the patient noncompliance query, the patient indication of noncompliance being a potential patient noncompliance indication selected among the plurality of potential patient noncompliance indications; and transmitting, on the mobile device processor, at least a portion of patient noncompliance information based on receipt of the patient indication of noncompliance with the treatment regimen and receipt of the plurality of compliance indications.

2. The method of claim 1, wherein receiving the treatment regimen comprises:
receiving a regimen selection of the treatment regimen from a plurality of available treatment regimens.

3. The method of claim 1, wherein receiving the treatment regimen comprises:
receiving an input indicative of the treatment regimen; and
querying a database including treatment regimen data based upon, at least in part, the input.

4. The method of claim 1, wherein receiving the treatment regimen comprises:
querying a database including electronic prescription data; and
receiving an indication of the treatment regimen from the database including electronic prescription data.

5. The method of claim 1, further comprising:
receiving a first treatment modification request; and
modifying the first treatment schedule in response to receipt of the first treatment modification request,
wherein scheduling the plurality of treatment events is based on a modified first treatment schedule.

6. The method of claim 1, further comprising:
receiving a preferred treatment time request,
wherein scheduling the treatment event of the plurality of treatment events in the electronic calendar is based upon, at least in part, receipt of the preferred treatment time request.

7. The method of claim 1, wherein the patient treatment alert includes a calendar reminder from the electronic calendar.

8. The method of claim 1, wherein the patient treatment alert includes a mobile device alert on a mobile electronic device associated with the device operator.

9. The method of claim 1, further including:
receiving a treatment diary entry; and
storing the treatment diary entry.

10. The method of claim 1, wherein the treatment regimen includes a multi- component treatment regimen, wherein the first treatment component includes a first treatment and the second treatment component include a second treatment different than the first treatment.

11. The method according to claim 1, wherein the treatment regimen includes a multi-component treatment regimen, wherein the first treatment component includes a treatment, and the second treatment component includes a dosing requirement.

12. The method of claim 1, further comprising:
generating a display including plurality of patient treatment questions associated with the treatment regimen, the treatment regimen associated with the management of a specific disease or ailment;
receiving an operator response to the plurality of patient treatment questions;
transmitting at least a portion of treatment diary information to a treatment management device, the treatment diary information based on the operator response.

13. The method of claim 1, wherein the patient intervention display further includes a warning regarding a consequence associated with the noncompliance.

14. The method of claim 1, wherein the portion of patient noncompliance information is de-identified prior to transmission.

15. The method of claim 1, wherein the portion of patient noncompliance information is transmitted to a treatment management device, the method further comprising:
receiving a patient intervention message from the treatment management device in response to transmission of the portion of patient noncompliance information, the patient intervention message being based on analysis of de-identified patient compliance information from a plurality of patients, the plurality of patients including the patient.

16. The method of claim 1, further comprising:
tracking an amount of compliance with the treatment regiment based on receipt of the plurality of compliance indications associated with the first treatment schedule and the second treatment schedule.

17. A non-transitory machine-readable medium comprising instructions, which when executed by one or more processors, cause the one or more processors to perform the following operations:
receive a treatment regimen associated with a patient, the treatment regimen being associated with treatment of a particular health condition of the patient and including a first treatment component and a second treatment component, and a first treatment schedule associated with the first treatment component and a second treatment schedule associated with the second treatment schedule;
schedule a plurality of treatment events in an electronic calendar, the plurality of treatment events scheduled to treat the particular health condition and based on the first treatment schedule and the second treatment schedule;
generate a plurality of patient treatment alerts, a patient treatment alert of the plurality of patient treatment alerts associated with a treatment event of the plurality of treatment events;
receive a plurality of compliance indications associated with the first treatment schedule and the second treatment schedule from a mobile device operator;
determine noncompliance with the first treatment schedule, the second treatment schedule, or both the first treatment schedule and the second treatment schedule based on receipt of the plurality of compliance indications;
generate a patient intervention display on the mobile electronic device associated with treatment of the particular health condition in response to a determination of the noncompliance, the patient intervention display including a patient noncompliance query and a plurality of potential patient noncompliance indications, the plurality of potential patient noncompliance indications including a personal non-availability indication, a no prescription drug available indication, and a prescription drug side effects indication;
receive a patient indication of noncompliance with the treatment regimen in response to the patient noncompliance query, the patient indication of noncompliance being a potential patient noncompliance indication selected among the plurality of potential patient noncompliance indications; and
transmit at least a portion of patient noncompliance information based on receipt of the patient indication of noncompliance with the treatment regimen and receipt of the plurality of compliance indications.

18. A system comprising:
a processor and a memory coupled to the processor;
a regimen module deployed in the memory and executed by the processor to receive a treatment regimen associated with a patient, the treatment regimen being associated with treatment of a particular health condition of the patient and including a first treatment component and a second treatment component, and a first treatment schedule associated with the first treatment component, and a second treatment schedule associated with the second treatment component;
a scheduling module deployed in the memory and executed by the processor to schedule a plurality of treatment events in an electronic calendar, the plurality of treatment events scheduled to treat the particular health condition and based on the first treatment schedule and the second treatment schedule;
an alert module deployed in the memory and executed by the processor to generate plurality of patient treatment alerts, a patient treatment alert of the plurality of patient treatment alerts associated with a treatment event of the plurality of treatment events; and
a compliance module deployed in the memory and executed by the processor to receive a plurality of compliance indications associated with the first treatment schedule and the second treatment schedule from a mobile device operator, determine noncompliance with the first treatment schedule, the second treatment schedule, or both the first treatment schedule and the second treatment schedule based on receipt of the plurality of compliance indications, generate a patient intervention display on the mobile electronic device associated with treatment of the particular health condition in response to a determination of the noncompliance, the patient intervention display including a patient noncompliance query and a plurality of potential patient noncompliance indications, the plurality of potential patient noncompliance indications including a personal non-availability indication, a no prescription drug available indication, and a prescription drug side effects indication, receive a patient indication of noncompliance with the treatment regimen in response to the patient noncompliance query, the patient indication of noncompliance being a potential patient noncompliance indication selected among the plurality of potential patient noncompliance indications, and transmit at least a portion of patient noncompliance information based on receipt of the patient indication of noncompliance with the treatment regimen and receipt of the plurality of compliance indications.

19. The system of claim 18, wherein the regimen module receives a regimen selection of the treatment regimen from a plurality of available treatment regimens.

* * * * *